United States Patent [19]

Draper et al.

[11] Patent Number: 5,496,698
[45] Date of Patent: Mar. 5, 1996

[54] METHOD OF ISOLATING RIBOZYME TARGETS

[75] Inventors: Kenneth G. Draper, Boulder; Dennis G. Macejak, Denver, both of Colo.

[73] Assignee: Ribozyme Pharmaceuticals, Inc., Boulder, Colo.

[21] Appl. No.: 987,130

[22] Filed: Dec. 7, 1992

Related U.S. Application Data

[63] Continuation-in-part of Ser. No. 935,854, Aug. 26, 1992, abandoned.

[51] Int. Cl.$^6$ ............................... C12Q 1/68; C12N 9/22
[52] U.S. Cl. ..................... 435/6; 435/91.31; 435/172.1; 435/172.3; 435/240.2; 435/320.1; 536/23.1; 536/23.2; 536/24.5; 514/44
[58] Field of Search ........................ 435/6, 91.31, 172.3, 435/172.1, 320.1, 240.1, 240.2, 91.4; 536/23.2, 23.1, 24.5; 514/44

[56] References Cited

FOREIGN PATENT DOCUMENTS

| | | |
|---|---|---|
| 9115580 | 10/1991 | WIPO . |
| 9118624 | 12/1991 | WIPO . |
| 9118625 | 12/1991 | WIPO . |
| 9118913 | 12/1991 | WIPO . |
| 9200080 | 1/1992 | WIPO . |
| 9201806 | 2/1992 | WIPO . |

OTHER PUBLICATIONS

Tabler et al. J. Cell. Biochem. Suppl. 15D, 1991, p. 21, CD 215.
Tabler et al. Gene (1991) 108:175–183.
Taylor, et al., "Ribozyme–Mediated Cleavage of an HIV–1 gag RNA: The Effects of Nontargeted Sequences and Secondary Structure on Ribozyme Cleavage Activity", 1 *Antisense Res and Dev* 173, 1991.
Sambrook, et al., "Molecular Cloning: A Laboratory Manual", published by Cold Spring Harbor Laboratory Press (N.Y.), pp. 7.71–7.78, 1989.
Scanlon et al., "Ribozyme–mediated cleavage of c–fos mRNA reduces gene expression of DNA synthesis enzymes and metallothionein", 88 *Proc. Natl. Acad. Sci.* 10591, 1991.
Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethionine tRNA", 109 *Jrnl of Amer. Chem. Society*, 7845, 1987.
Slim et al., "Configurationally Defined Phosphorothioate–Containing Oligoribonucleosides in the Study of the Mechanism of Cleavage of Hammerhead Ribozymes", 19 *Nucl Acids Res.* 1183, 1991.
Cameron et al., "Specific Gene Expression by Engineered Ribozymes in Monkey Cells", 86, *Proc Natl. Acad. Sci.* 1939, 1989.
Dropulic, et al., "Functional characterization of a U5 Ribozyme: Intracellular Suppression of Human Immunodeficiency Virus Type 1 Expression", 66 *Jrnl of Virol.* 1432, 1992.
Tsukiyama–Kohara et al., "Internal Ribosome Entry Site Within Hepatitis C Virus RNA", 66 *Jrnl of Virol.* 1476, 1992.
Perrotta and Been, 31 *Biochemistry* 16, 1992, "Cleavage of Oligoribonucleosides by a Ribozyme Derived from the Hepatitis δ Virus RNA Sequence".
Hampel and Tritz, 28 *Biochemistry* 4929, 1989, "RNA Catalytic Properties of the Minimum (–)sTRSV Sequence".
Hampel et al., 18 *Nucleic Acids Research* 299, 1990, "'Hairpin' Catalytic RNA Model: Evidence for Helices and Sequence Requirement for Substrate RNA".
Weerasinghe et al., 65 *Journal of Virology* 5531, 1991, "Resistance to Human Immunodeficiency Virus Type 1 (HIV–1) Infection in Human CD4$^+$ Lymphocyte–Derived Cell Lines Conferred by Using Retroviral Vectors Expressing an HIV–1 RNA–Specific Ribozyme".
Mamone et al., "Design of Hammerhead Ribozymes Targeted by Sequences in HIV, HSV, and the RAT ANF GENE", Abstract of Keystone, CO (May 27, 1992).
Pavco et al., "Regulation of Self–Splicing Reactions by Antisense RNA", Abstract of Keystone, CO (May 27, 1992).
Haseloff and Gerlach, 334 *Nature* 585, 1988, "Simple RNA Enzymes with New and Highly Specific Endoribonuclease Activities".
Guerrier–Takada et al., 35 *Cell* 849, 1983, "The RNA Moiety of Ribonuclease P Is the Catalytic Subunit of the Enzyme".
Robertson and Joyce, 344 *Nature* 467, 1990, "Selection In Vitro of an RNA Enzyme that Specifically Cleaves Single–Stranded DNA".

*Primary Examiner*—John L. LeGuyader
*Attorney, Agent, or Firm*—Lyon & Lyon

[57] ABSTRACT

Method for in vivo selection of a ribozyme active at a defined RNA target.

18 Claims, 2 Drawing Sheets

```
PRIMER-5'            REI         RANDOM SEQ    RIBOZYME
                                                  SEQ
5'-DDDDDDDDDDDDDDDD  RRRRRR  LLL  NNNNNNNN     CUGAUGAGGC

RANDOM SEQ      POLYADENYLATION
                                     REGION                    RE2
CGAAAGGCCGAAA        NNNNNNNN   LLL  AAAAAAAAAAAAAAAA_n  LLL   SSSSSS

PRIMER-3'
EEEEEEEEEEEEEEEEE-3'
```

METHOD OF ISOLATING RIBOZYME TARGETS

BACKGROUND OF THE INVENTION

This application is a continuation-in-part of Draper, U.S. Ser. No. 07/935,854, filed Aug. 26, 1992, now abandoned, entitled "In Vivo Selection of Ribozyme Targets," assigned to the same assignee as the present application, and hereby incorporated by reference herein.

This invention relates to methods for designing therapeutic ribozymes.

Robertson and Joyce, 344 *Nature* 467, 1990, describe in vitro selection of RNA enzymes.

Kramer et al., WO 92/01806, describe methods for optimizing cleavage of a target RNA by a ribozyme by selection of the most effective ribozyme in vivo. In general, a ribozyme is formed with a specific sequence complementary to a chosen target site and with a randomized sequence forming the enzymatic portion.

SUMMARY OF THE INVENTION

This invention features a method for constructing and selecting ribozymes, and in particular, amplifying vectors which express ribozymes in tissue culture systems. These ribozymes are selected for their ability to cleave a given target nucleic acid (e.g., RNA), and to inhibit the biological function of that molecule or any protein encoded by it. It is not necessary to know either the mRNA sequence of the target mRNA, or the intracellular localization of the ribozyme in order to select for active ribozyme constructs in this cellular system. This in vivo screening protocol (i.e., one which takes place inside a cell) offers many advantages over extracellular systems, because the synthesis of large quantities of RNA by enzymatic or chemical methods prior to assessing the efficacy of the ribozyme is not necessary.

Ribozymes are RNA molecules having an enzymatic activity which is able to repeatedly cleave other separate RNA molecules in a nucleotide base sequence specific manner. Such enzymatic RNA molecules can be targeted to virtually any RNA transcript, and efficient cleavage achieved in vitro. Kim et al., 84 *Proc. Natl. Acad. of Sci. USA* 8788, 1987, Haseloff and Gerlach, 334 *Nature* 585, 1988, Cech, 260 *JAMA* 3030, 1988, and Jefferies et al., 17 *Nucleic Acid Research* 1371, 1989.

Ribozymes act by first binding to a target RNA. Such binding occurs through the target RNA binding portion of a ribozyme, which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation), since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of an antisense oligonucleotide binding the same RNA site.

By "enzymatic RNA molecule" it is meant an RNA molecule which has complementarity in a substrate binding region to a specified gene target, and also has an enzymatic activity which is active to specifically cleave RNA in that target. That is, the enzymatic RNA molecule is able to intermolecularly cleave RNA and thereby inactivate a target RNA molecule. This complementarity functions to allow sufficient hybridization of the enzymatic RNA molecule to the target RNA to allow the cleavage to occur. 100% complementarity is preferred, but complementarity as low as 50–75% may also be useful in this invention.

In preferred embodiments, the enzymatic RNA molecule is formed in a hammerhead motif, but may also be formed in the motif of a hairpin, hepatitis delta virus, group I intron or RNAseP RNA (in association with an RNA guide sequence). Examples of such hammerhead motifs are described by Rossi et al., 8 *Aids Research and Human Retroviruses* 183, 1992, of hairpin motifs by Hampel et al., "RNA Catalyst for Cleaving Specific RNA Sequences", filed Sep. 20, 1989, which is a continuation-in-part of U.S. Ser. No. 07/247,100 filed Sep. 20, 1988, Hampel and Tritz, 28 *Biochemistry* 4929, 1989 and Hampel et al., 18 *Nucleic Acids Research* 299, 1990, and an example of the hepatitis delta virus motif is described by Perrotta and Been, 31 *Biochemistry* 16, 1992, of the RNAseP motif by Guerrier-Takada et al., 35 *Cell* 849, 1983, and of the group I intron by Cech et al., U.S. Pat. No. 4,987,071. These specific motifs are not limiting in the invention and those skilled in the art will recognize that all that is important in an enzymatic RNA molecule of this invention is that it has a specific substrate binding site which is complementary to one or more of the target gene RNA regions, and that it have nucleotide sequences within or surrounding that substrate binding site which impart an RNA cleaving activity to the molecule.

Applicant provides an in vivo system for selection of ribozymes targeted to a defined RNA target. The system allows many steps in a selection process for desired ribozymes to be bypassed. In this system, a population of ribozymes having different substrate binding arms (and thus active at different RNA sequences) is introduced into a population of cells including a target RNA molecule. The cells are designed such that only those cells which include a useful ribozyme will survive, or only those cells including a useful ribozyme will provide a detectable signal. In this way, a large population of randomly or non-randomly formed ribozyme molecules may be tested in an environment which is close to the true environment in which the ribozyme might be utilized as a therapeutic agent.

Thus, in a first aspect, the invention features a method for in vivo selection of a ribozyme active at a specific RNA target. In this method, a first population of ribozymes with differing substrate binding arms is introduced into a second population of cells which includes or is later caused to include the RNA target, and those cells which contain a ribozyme active at the target RNA identified.

In preferred embodiments, the ribozymes are encoded by an expression vector, and the method includes causing those ribozymes to be expressed from the vector in the cells. More preferably, the identified ribozyme is isolated and tested to determine activity in vivo; the RNA target is a viral RNA and the identifying step includes determining cell survival after infection by the viral RNA; the RNA target is a mammalian RNA and the cells are mammalian cells; the vector includes sequences encoding a 5' or 3', hairpin or a poly(A) tail for the ribozymes; the ribozyme is a hammerhead ribozyme with at least one substrate binding arm having between six and eight nucleotides; and the identifying step includes detecting expression of a reporter RNA attached to or regulated by the RNA target.

In more preferred embodiments, a ribozyme active at the RNA target is recloned into an amphitrophic retrovirus vector, and a retrovirus vector having or encoding the ribozyme is selected for ribozyme activity active at the RNA target.

In a related aspect, the invention features a population of nucleic acid molecules of the formula 5' NCNA 3', wherein each N is, or encodes, a ribozyme substrate binding arm, C is, or encodes, an enzymatic portion of a ribozyme, and A is an optional polyadenylation sequence; wherein at least one of the Ns in the population differs in each vector.

In preferred embodiments, the formula is 5' RNCNAS 3', wherein R and S are restriction endonuclease sites; the formula is 5' RLNCNLALS 3', wherein each L is nothing, or an insertion region which is or encodes a nuclear processing signal, an RNA stability signal, a splicing signal, or another nucleotide signal which effects transport or stability of the ribozyme molecule; the formula is 5' DRLCNLALSE 3', wherein D and E are defined nucleotide sequences which can be used to prime amplification of the nucleic acid molecule, or the complement of which can be used to prime amplification of the molecule.

In yet another aspect, the invention features a population of expression vectors each having one member of the population of nucleic acid molecules described above located within each vector, and a population of cells each having one member of the population of expression vectors present within each cell.

In another aspect, the invention features a ribozyme expression vector encoding a ribozyme and a hepatitis delta virus ribozyme motif, wherein the motif is able to cleave RNA including the ribozyme.

The invention also features construction of expression vectors for ribozymes for use in their selection in eucaryotic cells. These vectors are selected for their ability to express inhibitory ribozymes; a pluripotent cell line which is preselected for the maintenance of DNA containing ribozyme expression vectors; a method for the amplification of desired ribozyme-expressing regions, and the use of these regions or their equivalent for the therapeutic, diagnostic or prophylactic administration of ribozymes; and a method for targeting accessible sites within an mRNA which can be treated with either chemically synthesized ribozymes or ribozyme-containing transcripts.

Other features and advantages of the invention will be apparent from the following description of the preferred embodiments thereof, and from the claims.

DESCRIPTION OF THE PREFERRED EMBODIMENTS

The drawings will first briefly be described.

Figures 1, 2:
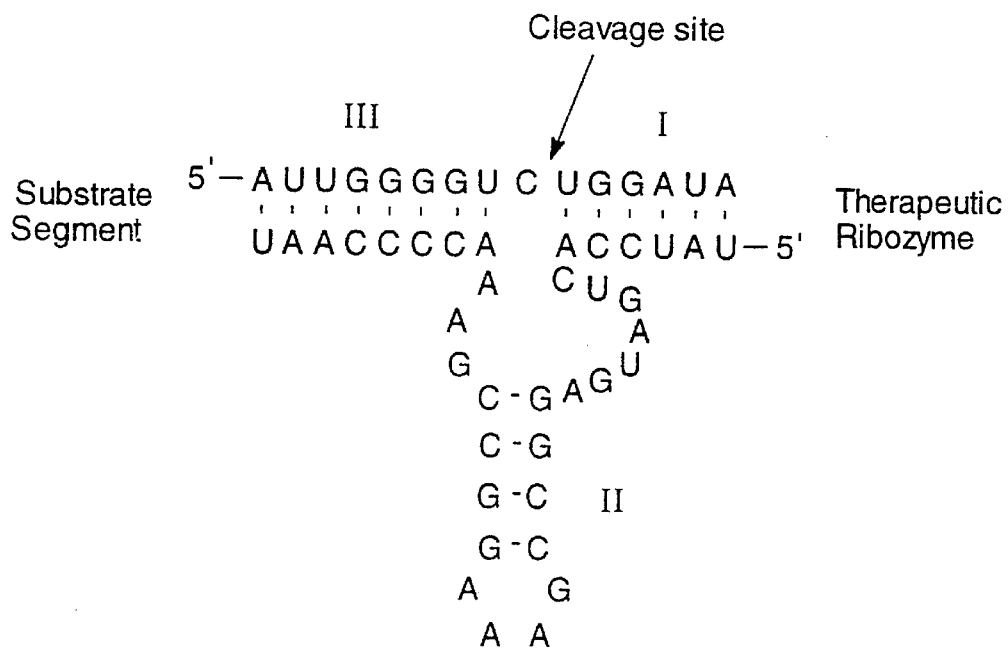

Drawings FIG. 1 is a diagrammatic representation of a hammerhead motif ribozyme showing stems I, II and III (marked (I), (II) and (III) respectively) interacting with a target region. The 5' and 3' ends of both ribozyme and target are shown. Dashes indicate base-paired nucleotides.

FIG. 2 is a diagrammatic representation of the ribozyme-coding strand of a DNA fragment prepared for insertion into an expression vector.

Figure 3:
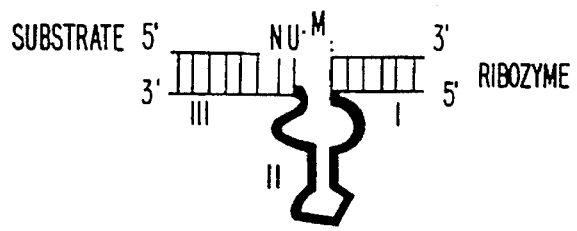

FIG. 3 is a diagrammatic representation of hammerhead ribozyme:substrate complex. N=G, A or C. M=U, A, C. Vertical lines represent intramolecular paired nucleotides between ribozyme and substrate molecules.

Figure 4:
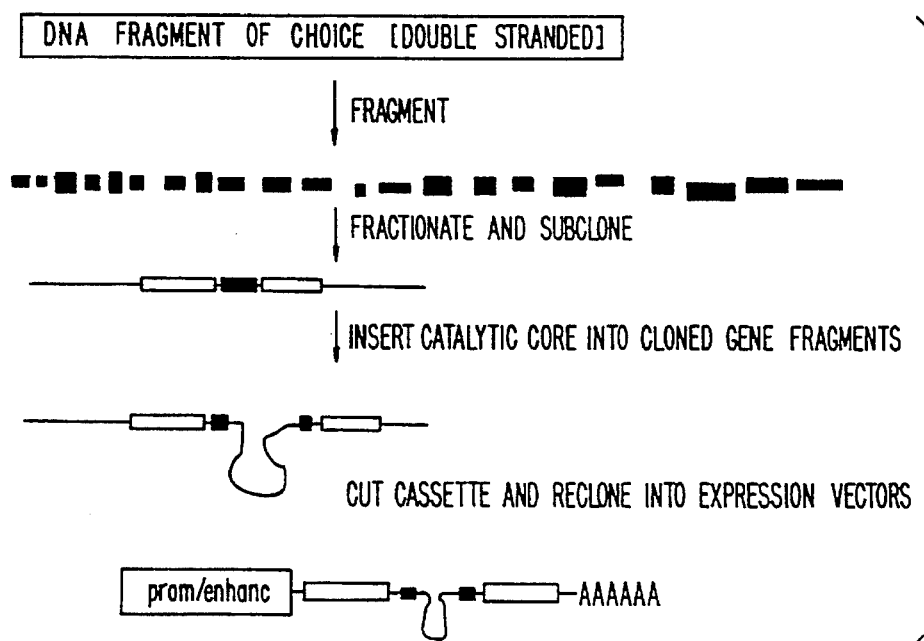

FIG. 4 is a flow diagram for cloning of quasi-random ribozyme cassettes.

Figure 5:
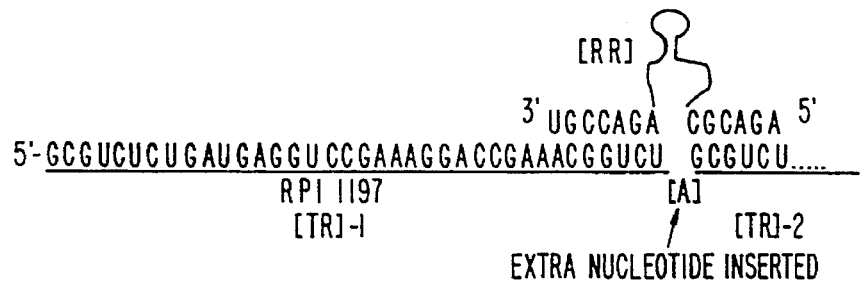

FIG. 5 is a diagram of the interaction between the releasing ribozyme (RR) and the therapeutic ribozyme (TR) cassette. (A) is an unpaired nucleotide between the TR concatamers which is required for effective RR cleaving activity. (TR)-1 and (TR)-2 are the first and second TR monomers released by RR cleavage.Ribozyme Population In general, to practice a method of this invention, it is necessary to generate a population of RNAs that have a high probability of containing the active ribozyme that is sought. It is also necessary to provide a method for selecting such an active ribozyme out of that population of RNAs. If desired, the population of RNAs can be formed with stabilizing structures, such as 3' and 5' hairpins, to protect the RNA molecules from nucleases. In addition, the RNA may be capped or a poly(A) tail provided. The ribozyme to be tested should be as small as possible to ensure that the possibility of misfolding of the ribozyme, or secondary structure formation deleterious to enzymatic activity, is reduced. Thus, the ribozyme should be formed with as little flanking sequence as possible, and any such flanking sequences should be provided in a form that ensures that it forms a hairpin at the end of the ribozyme sequence.

The length of a substrate binding arm of the ribozyme should be optimized so that it is not so short that an optimum ribozyme can never be found, and not so long that any extra sequence might fold upon itself and prevent binding. Long substrate binding arms are also less useful because they are more laborious to randomize. A shorter binding arm permits use of a suitable size population of ribozymes to be formed, screened, and tested. Substrate binding arms for a hammerhead ribozyme having between six and eight nucleotides in length is optimal; thus, for a hammerhead ribozyme if the substrate binding arm is eight nucleotides in length, with one invariant nucleotide at the 3' end of stem I, then only 15 positions need to be randomized to provide about $10^9$ ribozyme permutations.

Vector System

Once the generic structure of the ribozyme is chosen the position and identity of nucleotide variations can be selected by standard procedure. Generally, such ribozymes will be provided in a plasmid or other vector system. For example, such a vector may be a plasmid having a T7 promoter with the T7 RNA polymerase under the control of an inducible promoter to allow easy control of expression of the ribozyme. The promoter may be followed by a hairpin that helps to ensure proper operation of the T7 initiation sequence. A ribozyme-encoding DNA sequence may then be inserted upstream of these control regions, followed by a minimal T7 terminator hairpin to provide stability. Such a plasmid may be provided with a suitable restriction endonuclease site(s) to allow ready insertion of a population of random or otherwise synthesized ribozymes at the appropriate location.

In order to aid in generation of a population of ribozymes, it may be preferable to make a series of libraries that differ in the length of the substrate binding arms, and then mix those libraries together prior to transformation of a test cell. For example, 16 different libraries can be formed which have randomized substrate binding arms from 4 to 8 nucleotides on each side.

Selection

The selection strategy may take many forms. Preferably, the RNA that is targeted for cleavage should be in a configuration that is as close to "natural" as possible, so that the natural state of the target site will be accessible. If possible, selection should be carried out against full-length target RNA with no foreign flanking sequence. The target RNA also preferably is expressed in a cell that is its natural environment. For example, if the RNA is a mammalian RNA, a bacterial expression cell should be avoided since it is unlikely to contain the splicing factors and nuclear transport factors that bind to natural target eukaryotic mRNA. The selection system may have to be specifically chosen for each specific RNA target.

If the RNA target is a viral RNA, then the selection system can be devised to select for survival of a host cell after infection by that viral RNA. That is, a population of ribozymes are introduced into a host cell and those cells infected by the virus. Any cell which contains a ribozyme able to cleave the viral RNA will allow that cell to survive and grow. Thus, any growing cell potentially contains a desired ribozyme. It may be difficult to identify which viral gene is being cleaved by the selected ribozyme. While it may be important at some point to identify the target gene, it does not really matter which gene is targeted as long as the ribozyme actually works.

For other target RNAs it is possible to attach a reporter RNA to the end of the target RNA and to select for reduction in reporter-gene activity after ribozyme introduction. That is, a reporter DNA is ligated to DNA encoding the RNA target so that the two RNAs are produced as one RNA molecule. Cleavage of the RNA target can be designed to either activate or inactivate expression of the reporter RNA. If it is activated then a signal is provided in the cell (e.g., an enzyme activity such as β-galactosidase); if it is inactivated then the signal may be cell survival when the RNA encodes a toxic cell product (e.g., cholera toxin). This method permits ribozyme selection for one particular target RNA.

Any selected ribozymes will need to be screened to ensure that the reporter RNA is not the target of the ribozyme attack. In addition, they will need to be screened to ensure that the presence of any reporter RNA did not alter accessibility to the target RNA. That possibility can be readily checked in a subsequent screen involving the target RNA not attached to the reporter RNA.

If the RNA encoded by a regulatory gene is the RNA target, it is possible to place a reporter gene under the control of the target gene product. In that way a ribozyme can be selected against one particular RNA without worry about reporter RNA disrupting target RNA accessibility.

There follows examples useful in this invention by way of illustration. These examples are not limiting in the invention.

EXAMPLE 1

Synthesis and Construction of Random Ribozyme Coding Insert

The random ribozyme coding insert can be constructed by any number of methods which are appreciated by those skilled in the art. The following is but one method of synthesis which illustrates various essential and non-essential features of the insert.

The DNA fragments used for the insert are synthesized on an ABI 380B synthesizer according to the protocols supplied by the manufacturer. For the insertion of random nucleotides, four bottles which contain equimolar mixtures of monomers are sequentially sampled and the coupling and deprotection times are increased. These precautions will ensure the addition of the correct numbers of bases at these critical points in the construct. After synthesis, the DNA sequence of the mixture is end-labelled with $^{32}P$ and analyzed by Maxam and Gilbert analysis, or primed with radiolabeled complementary fragments which are extended and sequenced using a dideoxy sequencing method.

Referring to FIG. 1, there is shown one example of a ribozyme of the general hammerhead structure. The ribozyme population desired to select a useful ribozyme, however, has a randomized sequence in the regions which base pair with the target, i.e., the substrate binding arms.

The DNA sequence of the random ribozyme coding strand is synthesized first. One example is shown in FIG. 2, where $D_{17}$ is any defined nucleotide sequence which can be used to give effective priming for amplification of the sense strand of the DNA fragment; $E_{17}$ is the inverse complement of a defined nucleotide sequence ($F_{17}$) which can also be used to prime synthesis, but this time primes synthesis of the antisense strand of the fragment; $R_6$ and $S_6$ are restriction endonuclease recognition sequences for RE1 and RE2 enzymes, respectively; CUGAUGAGGCCGAAAGGCCGAAA is just one example of a core hammerhead ribozyme sequence for a hammerhead motif ribozyme; $N_8$ is a random substrate binding arm sequence of 8 nucleotides in length; $AAAAAAAAAAA_n$ is a polyadenylation region of undefined length; and each LLL is an optional insertion region which may be used to add nuclear processing signals, RNA stability signals, splicing signals or other such nucleotide signals which may effect the transport or stability of an expressed ribozyme molecule. Terminal sequences are chosen to have minimal homology between the 3' end of $D_{17}$ and the 5' end of $E_{17}$. RE1 and RE2 are any restriction endonuclease enzymes required for subsequent cloning procedures. The exact lengths of any of these regions may vary in different constructs, but the general structure and arrangement of the various regions is useful in this invention.

Because the terminal 3' nucleotide of the oligonucleotide is attached to the support for synthesis, it would be preferable to begin with an A-containing CpG bead and then extend the next 8 nucleotides of the 3' random binding arms, proceed with the core ribozyme (enzymatic) sequence, the 8 nucleotides of the 5' random binding arms, a restriction enzyme (RE1) recognition sequence ($R_6$), and end with a primer sequence ($D_{17}$) at the 5' terminus. Capping, uncoupling and deprotection would proceed by standard procedures.

The 3' termini of the random ribozyme coding sequences can be polyadenylated using poly(A) synthetase according to standard protocols. After the addition of the poly(A) tails at the 3' termini of the DNA fragments, the fragments can be partially purified by extraction, heat denatured and annealed to a nucleotide primer composed of the $D_{17}$ primer sequence at the 5' end, followed by a predetermined 6 nucleotide RE2 recognition sequence ($S_6$) and terminating in a $(dT)_{25}$ sequence.

Second strand synthesis is achieved by the addition of Taq DNA polymerase, appropriate salts and nucleotide substrates, and incubation for 16 minutes at 65° C. The resultant mixture contains double-stranded random ribozyme inserts which are composed of blunt-ended termini. The coding strands of these fragments contain the $D_{17}$ primer sequence, followed by the RE1 site, the random ribozyme coding sequence, a variable length poly(A) region, the RE2 site and an annealing region at the 3' terminus for the $F_{17}$ primer. These double-stranded fragments are amplified using Taq polymerase and appropriate DNA primer fragments ($D_{17}$ and $F_{17}$) prior to cloning into a desired vector.

Before ligation into the expression vector, the DNA mixture is digested with the restriction enzymes to create fragments containing defined 5' and 3' termini to allow cloning into the vector in a directional manner. The mixture is phenol extracted and purified by column chromatography to desalt and remove undesirable nucleotide fragments which are cleaved from the termini. Alternatively, the termini may contain a blunt end and subsequent cloning into an expression vector can be achieved after treating the DNA fragments with Klenow polymerase according to established protocols.

If desired, the polyadenylation sequence may be omitted, and the restriction enzyme primer or blunt end primer-containing regions complementary to the 3' regions of the random ribozyme coding strands can be used to initiate the synthesis of the second DNA strand. If either of the latter approaches are preferred, then the initial randomized ribozyme coding sequences should contain a common DNA sequence of 15–25 nucleotides at the 3' termini to facilitate second strand synthesis. This common DNA sequence may be complementary to a subset of the random sequences and may limit the utility of the described invention by base pairing with the ribozyme binding sequences and preventing the proper formation of ribozyme/substrate interactions.

It may be appreciated that the generation of random sequences in the binding regions of the ribozymes will also generate restriction endonuclease cleavage sites used to clone the DNAs into the vectors. Cleavage with the cognate restriction endonuclease may therefore result in the loss of any ribozyme constructs containing the given restriction enzyme recognition site. For this reason, each generation of construct libraries uses at least two dissimilar restriction enzyme sequences at the 5' and 3' termini (e.g., recognition sequences for Sal I and Pvu II are GTCGAC and CTGCAG, respectively). A series of fragments containing Eco RI sites at the 5' ends and either Pvu II or Sal I sites at the 3' ends, as well as fragments containing Eco RI sites at the 3' ends and either Sal I or Pvu II sites at the 5' ends creates ribozyme coding fragments with enough degeneracy in the coding regions to represent all possible nucleotide sequences in the expression vectors.

EXAMPLE 2

Construction of Ribozyme Expression Vectors

A number of suitable vectors for the expression of mRNA constructs in tissue culture and animals have been described in the literature, and may be used as effective vectors for the therapeutic expression of ribozymes. Stably transformed cell lines present the best test system for establishing parameters of expression which will be necessary for the development of optimal ribozyme-expressing vectors. Fragments of DNA can be easily introduced into these types of cells (e.g., HeLa cells) and selected for the maintenance of expression from the new fragments of DNA (e.g., by means of using the coexpression of a second gene which lends a selective advantage to the survival of the cell). Thus, for the effective construction of ribozyme expression vectors, a number of features may be built into the initial plasmid DNA construct; these include an eucaryotic transcriptional enhancer/promoter complex located immediately 5' to the ribozyme coding sequence, the presence of a hepatitis delta virus ribozyme motif located immediately 3' of the ribozyme coding sequence, the presence of a second coding sequence whose transcription is controlled by eucaryotic promoter and polyadenylation signal sequences, a bacterial origin of replication and an antibiotic resistance gene. The bacterial origin of replication and the antibiotic resistance genes are present to aid in growing the plasmid constructs prior to introduction into cell lines.

Many human transformed cell types express transacting factors which are capable of activating the SV40 early promoter region. For this reason, it is preferable to use an expression vector which contains the selection gene under transcriptional control of the SV40 early promoter. In cell types where the appropriate transcriptional activators are not ordinarily present, certain chemicals can be added exogenously to activate this promoter. Another preferred promoter is the metallothionein promoter which can be induced to activity by the addition of either glucocorticoids or heavy metal salts to the cells. Additional promoters which can be induced by endogenous or extracellular substances which are readily available to the cells are considered as alternative promoters in this invention. The ribozyme coding sequences may also be induced using the same promoter sequences as the selective gene, but the ribozyme construct can also utilize any promoter which is activated by a desired target disease condition (e.g., ribozymes targeted to inhibit specific viral gene expression, such as the herpes simplex virus ICP27 gene may utilize the same promoter as the viral gene, e.g., the ICP27 promoter). The preferable situation would involve a ribozyme gene operating under the promoter control of a very strong constitutive promoter such as the human cytomegalovirus immediate early region promoter (CMV ie1 promoter) or any of a number of housekeeping gene promoters (e.g., beta actin promoter). It is appreciated that many preferred promoters contain enhancer sequences within the DNA sequences required for optimal promoter activity. It is preferable to utilize promoters which contain natural enhancer sequences because the addition of certain enhancer-like regions upstream of some promoter regions may suppress the promoter activity.

Because extra nucleotides outside of the catalytic region in the ribozyme may cause the formation of secondary structures which would inactivate the enzymatic function of the molecule, the vector construct does not always contain intramolecular signaling sequences which are necessary for the correct polyadenylation of the transcript or termination of transcription. The poly(A) sequence which was introduced into the ribozyme construct will substitute for the polyadenylation signal, but the termination signal is an undefined sequence which is thought to be no less than 25 nucleotides in length. Instead of the termination signal sequence, each vector construct can have a hepatitis delta virus ribozyme sequence incorporated immediately 3' of the restriction enzyme cloning site at the 3' terminus of the ribozyme coding fragment described previously. This sequence is able to cleave the ribozyme transcript as transcription is proceeding past the region and will function as an artificial transcription terminator for the ribozyme transcript. The hepatitis delta ribozyme cleavage will leave one extra nucleotide 3' of the restriction enzyme insertion site (RE2). With certain restriction enzyme recognition sequences, it is possible to engineer the hepatitis delta ribozyme to cleave within the restriction site or at the 3'-terminus of the poly(A) stretch. The appropriate hepatitis delta virus (or hairpin or other ribozyme) ribozyme can be engineered into the expression vector immediately 3' of the RE2 site by standard insertion mutagenesis techniques.

After the appropriate expression vector is constructed and the random ribozyme insert is in place, the constructs must be stably introduced into cell lines for expression. The stable integration and expression is driven by the selective pressure imposed upon the cells by treatment with toxic chemicals, such as G418 (gentamicin) or hypoxanthine/puromycin/ thymidine (HPT) mixtures. The expression of neomycin resistance or thymidine kinase, respectively, will allow the transformed, expressing cells to survive and simultaneously afford the surviving cells the DNA needed to express transcripts from the random ribozyme genes introduced during transformation.

EXAMPLE 3

Stable Introduction of Ribozyme Expression Vectors Into Cell Lines

A number of methods to stably introduce DNA into cells are known in the literature, these include but are not limited by $Ca_2PO_4$ precipitation, DEAE dextran precipitation and electroporation. Generally, one microgram of DNA is applied to a 100 mm tissue culture dish containing subconfluent cultures of cells (approximately 3–4 million cells). Initially, at least 10 dishes will be transfected for each ribozyme DNA preparation. After an appropriate time is given for DNA uptake, the cells are rinsed in buffered medium and then refed with supplemented medium. In some cases, it may be preferable to include a glycerol shock step or the addition of inducing chemicals (e.g., glucocorticoid hormones or heavy metals to induce metallothionein promoter expression) to initiate the synthesis of selective gene products (e.g., thymidine kinase or neomycin resistance protein).

After 10–18 hours, the cells are trypsinized and replated in selective medium containing the toxic chemicals used for selection (e.g., 250–350 µM G418 in HeLa cells) against viable non-transfected cells. This medium may also contain chemicals required for the continued expression of any selective gene products necessary for cell survival. The continued presence of selective gene induction in the surviving cells may be required to maintain the ribozyme-containing plasmid because the transfected DNA is usually inherited as a unit which is maintained under the selective pressure used in the protocol. Often, when the selective pressure is removed, the foreign DNA is lost or deregulated in transformed cells. Because the cells will be maintained in the presence of chemical agents, care should be taken to avoid the use of agents which will interfere with subsequent ribozyme activity or introduction of infectious agents into the cell system.

Selected cells will be grown with medium changes every three days until confluent cultures are obtained. As the cells fill the tissue culture vessels, they will be trypsinized and transferred to larger vessels until cultures of between $10^{8-9}$ cells can be harvested for the preparation of frozen stocks. It is estimated that if each cell contains 1 nanogram of DNA, this will be 500 different ribozyme constructs if the average size of the plasmids is 7000 nucleotides. If the random ribozyme arms contain eight flanking nucleotides at each end for hybridization, this will give $4^{16}$ or $4.29 \times 10^{10}$ unique molecules. A total representation of these molecules should easily be found in $10^8$ cells if no more than 100 ribozyme constructs per cell is realized during the transfection/selection procedures. The expression of $4^{16}$ ribozymes within this cell culture should give sequences capable of hybridizing and cleaving virtually any unique mRNA sequence which can be targeted. It has been estimated that there are only $4^{12}$ unique RNA sequences expressed from the human genome. Clearly, any infectious agent would express a great deal less unique RNA sequences than can be targeted with these pluripotent ribozyme-expressing lines.

EXAMPLE 4

Selection of Therapeutic Ribozyme-Expressing Cells

There are many ways in which cells expressing therapeutically active ribozymes can be selected. In every case, the cells which express the desired ribozymes must be screened, cloned, and expanded for subcloning of the constructs into new vectors which allow the introduction of single copies of vectors into new cell lines. An example of an expression/selection protocol is given.

For this example, a ribozyme vector which is transcriptionally controlled by the HCMV ie1 promoter was used. This promoter is a very strong constitutively acting promoter which is controlled by transcriptional factors which are present in all cells. By using this promoter or any similar promoter, preinduction of transcription by hormones or chemicals is generally not required. Additionally, the HCMV ie1 promoter is transcriptionally activated by many factors which control genetic expression during infection of cells with heterologous viruses (e.g., the ie1 promoter is activated by the ICP4 and ICP0 proteins which control expression of herpes simplex virus [HSV] genes). Selective pressure which will kill all but the ribozyme expressing cells is presented as a viral infection (e.g., HSV infection of HeLa cells). This infection should be performed at a tissue culture infectious dose which will kill approximately 50% of the cells in one replicative cycle. The cells are treated with virus for three infectious cycles of the virus (three days for HSV-1) and then the RNA is harvested from a portion of the surviving cells to verify the expression of ribozyme molecules from the transcription vectors. Surviving cells are expanded for the preparation of frozen stocks. Stocks are prepared by standard methods. A culture of the resistant cells is grown for the preparation of DNA and a verification that the cells are resistant to infection with the target virus (e.g., verification of resistance will be determined by reinfecting the survivors with HSV-1).

EXAMPLE 5

Recloning of Ribozyme-Expressing Vector DNA

Resistant ribozyme-expressing cells selected by protocols described in the previous section will be expanded for the purpose of extracting the ribozyme cassettes which are expressed in these cells. Total cellular DNA will be isolated and purified from the cells by standard methods. The DNA preparation will be subjected to restriction enzyme digestion using enzymes capable of recognizing sites present in the expression vectors which are at least 50 nucleotides 5' and 3' of the ribozyme cassettes. By using this approach, the DNA sequences present upstream and downstream of the ribozyme cassettes are used to hybridize primer DNA fragments. After primer hybridization to the restricted DNA preparation, the ribozyme cassettes can be amplified by incubation with appropriate salts, nucleotide precursors and Taq polymerase (United States Biochemical Corp.) and incubation at 65° C. The resultant amplified DNA fragments can be electrophoretically separated from the other DNA fragments (unwanted cellular DNAs) in 2% agarose or other suitable matrix. The DNA cassettes are released from the amplified DNAs by digestion with restriction endonucleases which recognize the RE1 and RE2 sites used in the original cloning. A second agarose gel is run to purify the desired cassettes from the unwanted ends of the amplified DNA which correspond to expression vector sequences. The ribozyme cassettes are then cloned into appropriate amphitrophic retrovirus vectors using standard protocols.

These vectors should contain an inducible/selectable gene such as neomycin resistance and restriction enzyme cloning sites RE1 and RE2 which are downstream of an inducible or strong constitutive promoter. A protocol for packaging the recombinant DNAs into amphitrophic virus particles and transfection into cells is well known. Infection and selection of cells with these vectors will result in the incorporation of only one ribozyme vector per cell.

EXAMPLE 6

Reselection for Therapeutic Ribozyme-Expressing Cassettes

After cell lines are prepared which contain ribozyme expression cassettes within retrovirus vectors, the cells are again selected for the expression of ribozymes which protect the cells from infectious agents, or prevent expression of an undesirable genetic trait. The selection protocol is similar to that described for the first selection (i.e., infection with HSV-1 at appropriate concentrations of virus, growth for three viral replicative cycles, and clonal expansion of any surviving cells). After stock cells are prepared, the cells are rechecked for viral resistance and the retroviral vector is induced to replicate by standard methods (e.g., chemical treatment). Viral particles are isolated and the sequences of the therapeutic ribozymes are determined by direct sequencing of the viral genomes. Molecular methods of inducing retroviral replication, isolation of particles and sequencing of the genomes are known to those in the art.

Once the sequence of a therapeutic ribozyme has been determined by the methods described herein, the ribozyme can either be incorporated into an expression vector for in vitro synthesis, or genetic therapy, or the ribozyme can be synthesized chemically for use with exogenous delivery techniques. Descriptions of useful systems are provided in the art cited above, all of which is hereby incorporated by reference herein.

Quasi Random Methods

The following are examples methods of cloning quasi-random ribozymes into expression vectors, in vitro assays for optimizing ribozyme structural features which yield favorable catalytic activity, and methods of cloning concatameric ribozymes into an expression vector.

The techniques described below may be used to find effective therapeutic ribozymes to any desired target RNA even if the exact location of the transcript within a gene is uncertain. Methods are described whereby the selected ribozyme may be optimized for catalytic activity using cellular extracts for in vitro assays. Four vectors are described which allow the cloning of quasi-random ribozymes into plasmids and facilitate the excision of selected ribozyme cassettes for cloning into a eucaryotic expression vector for intracellular assays of ribozyme cleavage activity. A method is described which allows for the cloning of concatameric ribozyme cassettes into expression vectors and thereby results in a more effective ribozyme-expressing vector for use in cellular applications of genetic or therapeutic interest.

EXAMPLE 7

Cloning of Quasi-random Ribozymes

Four novel cloning vehicles were constructed for the generation of quasi-random ribozymes. The herpes simplex virus thymidine kinase (TK; Wagner et al, 1981, Proc. Natl. Acad. Sci. U.S.A. 78: 1441–1445) gene was used as a prototype gene target for the cloning. Methods for the generation of the cloning vehicles, insertion of the TK DNA fragments and incorporation of a hammerhed ribozyme motif into the constructs follow. Use of this method allows one to clone target-specific ribozymes from any fragment of DNA, even when the primary DNA sequence or direction and dimensions of mRNA coding regions are uncertain. The subsequent use of biological selection and amplification of the desired clones will generate ribozyme constructs which have potentially advantageous genetic or therapeutic activities.

The basic requirement of the cloning vector in this protocol is that the restriction endonuclease site located immediately 5' of the cloned target DNA sequences be recognized by a restriction enzyme which cleaves the target DNA at a distance (x nucleotides) 3' of the recognition sequence. The distance (x) between the recognition and cleavage sites (along with the size of DNA fragments selected for cloning) will dictate the length of the ribozyme binding arms in the quasi-random constructs. The cloning of hammerhead ribozyme catalytic sequences into the inserted DNA fragments is facilitated greatly by using restriction enzymes that cleave to yield overhanging 3' ends which are 2 nucleotides in length. The cloning protocol deletes these two bases and inserts a ribozyme catalytic core at the site of the restriction enzyme cleavage. Use of restriction sites which give 5' overhangs, blunt ended fragments or 1 nucleotide 3' overhanging ends result in the generation of flanking sequences which no longer reflect the original DNA sequence or ribozymes which do not allow for the unpaired base (M) in the RNA substrate which is required for effective hammerhead ribozyme cleavage. See FIGS. 3 and 4.

Cloning sites were constructed so that the ribozyme expression cassettes could be excised from the original plasmid vectors and inserted into eucaryotic expression vectors. Because restriction endonuclease sites will exist in the random fragments of target DNA, multiple releasing and core insertion cleavage sites should be available for each series of constructs. By using constructs with different releasing and core insertion restriction endonuclease sites, one can be relatively confident of acquiring all random ribozyme recognition sites with only four cloning vehicles. Two cloning inserts were designed for use in PGEM4 and pSP72 (Promega Corp; Madison, Wis.) vectors. For the PGEM4 vectors, BpmI/SmaI and BsgI/SmaI cloning sequences were flanked at the 5' and 3' ends by HindIII and EcoRI restriction endonuclease sites, respectively. For the pSP72 vectors, the 5' and 3' flanking restriction endonuclease sites were BglII and XhoI, respectively. Each of these vectors contains a T7 and SP6 promoter region at the 5' and 3' terminus of the cloning sites, respectively. The phage RNA polymerase promoters allow in vitro transcription of the ribozyme inserts and testing of ribozyme activity prior to the insertion into eucaryotic expression vectors.

The four pairs of DNA oligonucleotides (Midland certified Reagent Co.; Midland, Tex.) used to clone into the PGEM4 and pSP72 vectors were:

```
(A) 5'  AGCTTCTGGAGCCCGGG        3'
    3'        AGACCTCGGGCCCTTAA  5'

(B) 5'  GATCTCTGGAGCCCGGGC       3'
    3'        AGACCTCGGGCCCGAGCT 5'

(C) 5'  AGCTTGTGCAGCCCGGG        3'
    3'        ACACGTCGGGCCCTTAA  5'

(D) 5'  GATCTGTGCAGCCCGGGC       3'
    3'        ACACGTCGGGCCCGAGCT 5'
```

Pairs A and C were cloned into PGEM4 and pairs B and D were cloned into pSP72. To incorporate the cloning inserts into the plasmids, 10 µg of each oligonucleotide was combined with its paired oligonucleotide in a 1:1 ratio and incubated in TMN solution (50 mM Tris-HCl, pH 8; 10 mM MgCl$_2$, and 100 mM NaCl) at 90° C. for 2 min, then slowly cooled to 25° C. One tenth (2 µg) of the annealed mixture was ligated to the appropriate linearized vector fragments. Prior to addition to the ligation reaction, vector DNA was digested with the appropriate restriction enzymes (HindIII/EcoRI for PGEM4 and BglII/XhoI for pSP72) and the linearized fragments were isolated from low melting point agarose as described by Maniatis et al, 1982, Molecular Cloning: A Laboratory Manual. Cold Spring Harbor Laboratory, Cold Spring Harbor, N.Y. Ligations were performed at 14° C. for 18–24 h in 20 µl total volume. Buffer was as suggested by the manufacturer (United States Biochemical Corp.[USB]; Cleveland, Ohio). After ligation of inserts into the vectors, bacteria (HB101) were transformed at 37° C. for 20 min with approximately 100 ng of vector DNA (one tenth of the reaction volume, 2 µl). Colonies of bacteria were selected on agarose plates containing ampicillin and then amplified in 3 ml cultures for identification of appropriate cloning vehicles. The presence of cloning inserts into PGEM4 and pSP72 vectors was analyzed by restriction endonuclease digestion of the plasmid DNA preparations. Samples of appropriately transformed bacteria were identified and 250 ml cultures of the bacteria were grown. Plasmid DNA was purified from the 250 ml cultures using QIAGEN columns (QIAGEN, Inc.; Chatsworth, Calif.) and protocols suggested by the manufacturer. Each of the four plasmid vectors generated in this manner were used in a similar protocol to clone random DNA inserts of the herpes simplex virus thymidine kinase (TK) gene.

For cloning of the TK gene fragments, 50 µg of the TK DNA (2.7 kb EcoRI fragment N) was excised by EcoRI/ScaI digestion of plasmid DNA containing this fragment. The ScaI digestion was incorporated to remove the plasmid bands of pSP72 which is also 2.7 kb in length. EcoRI fragment N was isolated by electrophoresis in low melting point agarose and subsequent elution by standard protocols (Maniatis et al, 1982). After isolation and concentration by ethanol/salt precipitation, the EcoRI fragment N DNA was fragmented by limited digestion with DNase I. The digestion was performed by combining 20 ug of TK DNA and 2 units of DNase I (USB) in 200 µl of total volume containing 50 mM Tris-HCl, pH 7.5; 10 mM MgCl$_2$, and 10 µg bovine serum albumin (BSA). The mixture was incubated at 37° C. and 50 µl aliquots were removed and combined with 5 µl of 0.5M EDTA after 1, 2.5, 5 and 10 min. All reaction aliquots were electrophoresed in 8% polyacrylamide gels to size fractionate the pieces. Fragments 20–40 nucleotides in length were cut from the gels and eluted according to the methods of Maniatis et al, 1982. The digestion protocol is dependent upon the base composition of the DNA and should be optimized for each fragment which is to be digested. We found that the optimum digestion time for the HSV TK gene was approximately 2.5 min. The termini of the eluted DNA fragments were repaired with Klenow fragment of DNA polymerase to generate blunt ended fragments for cloning into the plasmid cloning vehicles described above. The repair reactions were performed in 20 µl volumes at room temperature for 1 hour according to protocols described by the manufacturer (USB).

After repair of the termini, the DNA fragments were dephosphorylated by incubation with calf alkaline phosphatase enzyme (CIP, United States Biochemical Corp.) and the fragments were prepared for insertion into cloning vectors by extraction in phenol/chloroform/isoamyl alcohol mixtures(24:24:1) and ethanol precipitation. Ten micrograms of each cloning vehicle was linearized by digestion with SmaI restriction endonuclease and the linearized fragments were electrophoresed in 1% low melting point agarose gels to remove the fraction of undigested vectors. Elution from the agarose was as descibed by manufacturer. One microgram of vector was combined with one microgram of DNA fragment preparation (1:100 molar ratio of vector to insert, respectively) and then fragments were ligated in a total volume of 20 µl at 25° C. for 18–24 h. Prior to transformation of bacteria, the ligation mixture was digested with XmaI restriction endonuclease (5 units of enzyme in 20 ul volume for 3 h) to relinearize vector pieces which had closed during ligation. (Xma1 is an isoschizimer of SmaI.) The digested preparations were then transformed into HB101 cells as described earlier. The resultant populations of ampicillin resistant bacteria were grown in a batch culture to recover all plasmid vehicles for the insertion of the ribozyme catalytic core sequences into the TK DNA fragments.

Prior to cloning the ribozyme catalytic core into the TK DNA fragments, plasmids were linearized by digestion with appropriate enzymes (BpmI or BsgI; New England Biolabs; Beverly, Mass.) and the linearized plasmids were isolated after electrophoresis in low melting point agarose gels. The linearized preparations were digested with T4 DNA polymerase to generate blunt ends and the DNAs were dephosphorylated by treatment with CIP enzyme. After phenol/chloroform/isoamyl alcohol extraction, the DNA fragments were precipitated with ethanol and resuspended in TE buffer (10 mM Tris-HCl, pH 7.5; 1 mM EDTA). The catalytic core sequence was inserted into the linearized plasmid DNA by annealing the following oligonucleotides as described above:

```
5'  CTGATGAGGCCGAAAGGCCGAAA     3'
3'  GACTAACTCCGGCTTTCCGGCTTT    5'
```

After annealing, 0.1 µg of the oligonucleotide mixture was added to 1 µg of the blunt-ended, linearized plasmid preparation (gives a 10:1 molar ratio of insert:vector sequences) in ligation buffer to give a final reaction volume of 20 µl. The mixture was incubated overnight at 16° C. and then one tenth of the total volume (2 µl) was added to 100 µl of transformation solution containing HB101 cells. After transformation of the cells, 10 ml preparations of the bacteria were grown and plasmid DNA was isolated from 5 ml of the preparation as described in a previous section. The remaining 5 ml of bacteria was divided among three tubes, combined with an equal volume of 40% glycerol and frozen at −80° C. for stock solutions.

Use of the quasi-random ribozyme cloning generates gene fragments and catalytic cores which are present in both sense and antisense orientations. Because ribozymes will be created which cleave transcripts from both strands of the DNA fragment, this mixture of inserts is advantageous when cell selection of ribozyme activity is sought and the direction of transcription within the target DNA is unknown. The random insertion method should result in a 1:1 mixture of sense strand and complementary strand cleaving ribozymes. The presence of RNA polymerase promoters at both ends of the DNA insertions allows versatility in the choice of transcription protocols (because roughly equal distributions of ribozyme structures and specificities should be obtained with either series of trancsripts) and compensates for non-random directional insetions into the vector.

For a cursory examination of catalytic activity within the quasi-random ribozyme populations, in vitro transcripts were synthesized from the plasmid DNA templates prepared above. The plasmid DNA preparation was split into two fractions (the yield of DNA was approximately 10 µg in each fraction) for digestion with restriction endonucleases and in vitro transcription with either T7 or SP6 RNA polymerase. The PGEM4 based plasmids were cleaved with Eco RI for T7 transcriptions and with HindIII for the SP6 transcriptions. The pSP72 based plasmids were cleaved with XhoI for T7 transcriptions and with BglII for the SP6 transcriptions. One microgram of linearized DNA template was added to a transcription mixture containing 20 µl of 5× buffer (200 mM Tris-HCl, pH 7.5; 50 mM MgCl$_2$; 10 mM spermidine and 50 mMNaCl), 10 µl of 100 mM dithiothreitol (DTT); 5 µl of RNasin (20,000 U/ml; GIBCO/BRL, Gaithersburg, Md.); 5 µl of NTP mixture (20 mM each of ATP, GTP, CTP and UTP) and enough water to bring the final volume to 95 µl. 100 units of T7 or SP6 RNA polymerase (USB) was added and the mixture was incubated at 37° C. for 1 h, after which RNase-free DNAse I was added and the reaction was incubated an additional 15 min at 37° C. The solution was brought to a volume of 150 µl, extracted once with phenol/chloroform/isoamyl alcohol and subjected to spin chromatography through a 1 ml bed volume of G-50 Sephadex (Pharmacia, Upsalia). A typical transcription yields 10–15 µg of RNA per µg of DNA template.

For the synthesis of $^{32}$P-labeled TK substrate RNA, template DNA was prepared by PCR amplification using primers 5' TAAT ACGACT CACT AT AGGGACCGAGCGACCCT GCAG 3' and

5' GCC GT CAT AGC GC GGGT which resulted in the generation of double-stranded DNA template containing a T7 RNA polymerase promoter region located immediately 5' of the TK mRNA coding sequences (1262 nucleotides). The transcription reaction was essentially as described for ribozyme synthesis except that the total reaction volume was decreased to 20 µl, contained only 20 units of T7 polymerase and the 1 µl of 20 mM NTPs was substituted with 1 µl of 20 mM ATP, GTP and UTP, 1 µl of 2 mM CTP and 2 µl of α-$^{32}$P-CTP (80 µCi; 800 Ci/mmol; Dupont/NEN; Boston, Mass.). TK RNA was purified by spin chromatography through G-50 Sephadex columns. When ill-defined target DNA is used as the source of insert fragments, template for the transcription of target RNA may be prepared by blunt-end ligation of the DNA into pSP72, PGEM4 or other suitable transcription vectors.

For analysis of ribozyme cleavage of the TK transcript, the in vitro transcripts were mixed with 50,000 cpm of in vitro transcribed TK RNA and incubated at 37° C. in a total volume of 50 µl containing 5 ul of 10× ribozyme cleavage buffer (750 mM Tris, pH 7.5, and 100 mM MgCl$_2$) and a final ribozyme concentration varying between 0.1 and 10 µM. Control reactions contained 10 ng of yeast tRNA instead of the ribozyme mixture. At given time intervals, aliquots were removed and quenched by addition to a solution containing (20 mM EDTA, 95% formamide and 0.1% Bromphenol Blue and Xylene Cyanol). Samples were heated at 90° C. for 10 min, snap cooled in ice and cleavage products of the TK RNA were identified by electrophoresis of the samples in 3% polyacrylamide gels and subsequent visualization of cleaved RNA fragments by autoradiography. DNA preparations whose transcripts exhibited ribozyme activities specific for the TK RNA were amplified by growing 250 ml cultures of the parent bacterial stocks. The plasmid DNA islated from these stocks was digested with either HindIII/EcoRI or BglII/XhoI restriction enzyme combinations and the released ribozyme coding sequences were isolated by gel electrophoresis and cloned into appropriate eucaryotic expression vectors for use in tissue culture experiments.

The screening and identification of ribozyme vectors which cleave target RNA intracellularly is tedious and depends upon the choice of target mRNA whose expression lends a negative selective advantage to the cells (e.g. HSV TK expression will render cells sensitive to treatment with acycloguanosine [ACV]). By growing TK-expressing cells in the presence of ACV and ribozyme-expression vectors, one may select and expand only the cells containing inhibitory ribozymes. The DNA encoding effective ribozymes may be extracted and PCR amplified by standard methods because the flanking regions within the eucaryotic expression vectors will be known. After identification of effective ribozyme sequences, the ribozyme structures may be optimized by the following in vitro methods prior to insertion into appropriate therapeutic expression vectors.

EXAMPLE 8

In Vitro Ribozyme Optimization

An adjunct approach to cell-based selection of effective quasi-random ribozyme constructs uses a modification of the in vitro ribozyme activity assay described in the previous section. When uniformly labeled transcript is used to check ribozyme activity, multiple cleavages within the transcript prevent the identification of susceptible RNA structures. For any given quasi-random population of ribozymes, the number of possible ribozyme molecules is approximately 2(x−y)/4, where x is the length of one strand of DNA and y is the average length of the DNA fragments inserted into the vectors. Because the length of ribozyme binding arms is small compared to the sizes of most genes, the number of ribozymes screened will be approximately one-half the number of nucleotides in the coding strand of the DNA. For the 2.7 kb piece of TK DNA, one expects approximately 1350 ribozymes (approximately 632 ribozymes nucleotides in the TK coding region). Many of these ribozymes will target inaccessible structures within the target mRNA or possess incompatible secondary structures which will reduce their catalytic activity.

To determine the limited sites within the RNA which are accessible to active ribozymes, it is preferable to assay ribozyme activity using substrates with uniquely labeled sites (5' or 3' end-labeled). Analysis of the cleaved substrate fragment size will give an approximate location within the substrate where ribozyme cleavage occurs. By using different sizes of substrates spanning the target RNA, one may localize most of the preferred ribozyme target sites to defined distances from the 3' or 5' ends of the target RNA. Sequencing of the DNA template in these regions will reveal the probable ribozyme recognition sequence, which can be verified by synthesizing 20–40 mers of the substrate RNA and testing for cleavage in the presence of the quasi-random ribozyme preparation. Synthesis of RNA molecules in this size range may be accomplished enzymatically or chemically by established protocols.

After the target region has been identified, ribozymes to the target sequence may be synthesized which contain sequence modifications or additions which increase catalytic rates or nuclease stability in cellular extracts and/or alter intracellular localization when synthesized in transient assays from eucaryotic expression vectors. A reproducible, simple technique for assaying ribozyme cleavage of target RNAs in cellular extracts is described below.

DNA templates for the synthesis of antisense RNA probes spanning the TK gene were amplified from 10 ng of HSV-1 (KOS strain) DNA, using the following primers:

PRIMER A    5'   T AAT ACG ACT CAC T AT AGG GCT TCT TGC T GC CCG GCG A   3'

PRIMER B    5'   CAT CCC CGT GGC CCG TT   3'

Primer A contains a T7 RNA polymerase promoter. Probes with a specific activity of $1.8 \times 10^6$ dpm/ng were synthesized directly from PCR-amplified template DNA using T7 RNA polymerase (USB) as described by the manufacturer, in the presence of $^{32}$P-labeled CTP (Dupont/NEN). Cytoplasmic extracts (40 µl) derived from HSV-infected Vero cells (MOI=1, HSV-1, strain KOS) were combined with 5 µl of 10× ribozyme cleavage buffer (750 mM Tris, pH 7.5, and 100 mM MgCl$_2$) and ribozyme (diluted in 5 µl water, final ribozyme concentration varied from 0.1 to 10 µM), and incubated at 37° C. for varying amounts of time. Following ribozyme cleavage, extracts were diluted to 400 µl with 4M guanidine thiocyanate lysis buffer and RNA was extracted as described (Chomszynski and Sacchi, 162 *Anal. Biochem.* 156, 1987). RNA was resuspended in 45 µl lysis buffer, antisense TK probe (1–5×10$^5$ cpm in 5 µl lysis buffer) spanning the cleavage site was added, then hybridization reactions were overlayed with 30 µl of mineral oil and incubated at 55° C. for 18–20 hours. After hybridization, 500 µl of RNAse solution (0.4M NaCl, 20 U/ml RNase A, 2 U/ml RNAse T1 and 10 mM Tris/HCl pH 7.5) was added, and reactions were incubated at 37° C. for 30 minutes. Following nuclease digestion, 10 µl of 20% SDS and 10 µl of 20 mg/ml proteinase K were added, the reactions were heated an additional 30 minutes at 37° C., and hybrids were precipitated with 500 µl of isopropanol. Pellets were resuspended in 10 µl of solution containing 95% formamide, 10 mM EDTA, 0.1% bromophenol blue and 0.1% xylene cylanol (USB), heated to 95° C. for 4 minutes, then loaded onto 5% polyacrylamide/7M urea gels and electrophoresed at 65 W constant power. Gels were dried and the radioactivity corresponding to protected RNA fragments was visualized by autoradiography and quantified using an AMBIS detector.

EXAMPLE 9

Cloning of a Concatameric Ribozyme Construct

After ribozymes have been selected for effective cleavage of target RNA in cells or extracts and optimized for catalytic rate, intracellular stability and subcellular localization, the final step in designing efficient ribozyme-expression vectors involves the cloning of multiple therapeutic ribozymes (TRs) within the transcription unit. The release of the TRs from the transcript necessitates the cloning of an additional releasing ribozyme (RR) which can cleave between TR units in the nascent transcripts.

To test the concatameric ribozyme vector construction, we chose a ribozyme targeted to the HSV-1 ICP4 mRNA. This ribozyme (RPI 1197) was chosen because it has been extensively characterized enzymatically using both short and long RNA substrates ($K_{cat}/K_m = 4 \times 10^7$ and $3 \times 10^4$ mole$^-$1/min$^{-1}$, respectively) and has been used in tissue culture studies to inhibit the replication of herpes simplex virus. These data afford us important catalytic and therapeutic values to which we can compare ribozyme activities observed with a concatameric vector.

After choosing the TR, RR must be designed which is capable of cleaving tail-to-head concatamers of the TR. As shown in FIG. 5, the sequence of RPI 1197 made design of a RR very easy because insertion of one nucleotide (A) between the concatamers gave a good ribozyme target site. We have found that extension of the arms of hammerhead ribozymes by one or two nucleotides does not reduce the catalytic activity significantly (usually <30%). This allows some flexibility in designing the TR monomers to accomodate extra nucleotides which optimize the sequence of the RR cleavage site. If the sequence cannot be manipulated using nucleotides present in the gene, it is preferable to place a UM sequence at the 3' end of the TR, where M=C, U or A. This modification of the sequence will give a UM trinucleotide of unpaired bases when the TR hybridizes to target RNA. Unpaired nucleotides at the 3' termini of hammerhead ribozymes usually reduce catalytic activity only when they force the ribozyme into altered structures which are more stable than the enzyme-substrate complex. A preliminary check to detect such unfavorable structures can be performed using computer-based RNA folding algorithms.

If additional sequences such as cytoplasmic localization signals or polyadenylation signals are desired in the TR, these sequences should be considered when designing the RR. Our cloning protocol may be used to incorporate these structures at either terminus of the TR, but we have found that many additional sequences interfere with proper folding of the TR. Exceptions to this observation are the sequences which have strong internal base-pairing, such as hairpin loops or tRNA motifs.

After deciding upon the sequence of the RR motif, it is preferable but not necessary to determine if the RR will cleave the tail-to-head concatameric TR junction. This may be accomplished by synthesizing substrate and ribozyme RNA, as described previously, then performing cleavage reactions in the presence of 10 mM $Mg^{+2}$. After verifying the catalytic activity of the RR, the RR motif is cloned into an appropriate vector which contains multiple cloning sites 3' of a phage promoter. For this cloning step, we chose to use PTZ19R (USB). By using a directional cloning protocol, the screening required consists of restriction digests of the isolated plasmid DNA. Without a directional protocol, the small size of the RR inserts would necessitate sequencing of the plasmid DNA to choose correct clones, except in the rare cases where the stem I or stem III regions (see FIG. 3) contain a convenient, diagnostic restriction endonuclease recognition site.

Cloning of the RR fragment into PTZ19R used the two oligonucleotides, 5'-CCCAAGCTTGTCGCCTGATGAG-GTCCGAAAGGA-3' and 5'-CCCGTCGACGGTCTTTCG-GTCCTTTCGGACCTC-3', which will create the RR coding sequence flanked by HindIII and SalI restriction endonuclease sites (bold faced type) at the 5' and 3' termini, respectively. Four microgram samples of each oligonucleotide were added to a reaction mixture containing 4 μl of 10× SEQUENASE buffer, 4 μl of 2.5 mM dNTP, 4 μl of 0.1M DTT, and 1.5 μl of SEQUENASE polymerase (20U, USB) in a total volume of 40 μl. After the mixture was incubated at 37° C. for 1 hour, a 5 μl aliquot was removed and added to 5 μl of loading buffer prior to electrophoresis in 10% polyacrylamide gels. Bands were visualized by staining with Stains-all (USB). The remainder of the sample was frozen at −20° C. After verification that the appropriate fragment was generated, 5 μl of the frozen mixture was added to a 15 μl mixture containing 10 U each of SalI and Hind III restriction endonucleases, 1.3× restriction endonuclease buffer, and 10 U of shrimp alkaline phosphatase (USB) and the final mixture was incubated at 37° C. for 1 hour before phenol/chloroform/isoamyl alcohol extraction and precipitation of the DNA with ethanol. The pellet was dissolved in water and 30 ng of the insert DNA fragment was added to 300 ng of PTZ19R DNA fragment which had been digested with Hind III and Sal I enzymes then gel isolated in low melting point agarose. This plasmid (PTZ19R):insert concentration gave an approximate molar ratio of 1:10, respectively. The DNA samples were added to ligation buffer and ligated with T4 DNA ligase (USB) at room temperature for 2 hours, then at 4° C. for 18 hours. One-half of the ligation mixture (8 μl) was transfected into 100 μl of competent DH5α-*E. coli* cells (GIBCO/BRL) and plated onto LB agar plates containing ampicillin. Six clones were picked from the plates and grown in 10 ml overnight preparations for the extraction and restriction enzyme digestion of the plasmid DNA. The insertion of the RR DNA was verified by the increase in plasmid DNA size when digested with either Hind III or Sal I enzymes and by the disappearance of the Pst I site which was replaced in the PTZ19R vector with the RR coding DNA. A 250 ml preparation of bacteria transformed with the new RR-containing plasmid was grown and the plasmid DNA isolated was digested with Sal I and Bam HI restriction enzymes prior to use as the vector for subsequent cloning of the concatameric TR inserts.

Four oligonucleotides were synthesized for use in the TR concatamer cloning. The oligos were:

TRS    5'GCGTCTCTGATGAGGTCCGAAAGGACCGAAACGGTCTA

TRC    5'CATCAGAGACGCTAGACCGTTTCGG

TRSS   5'GGGTCGACGCGTCTCTGATGAGGTCCGAAAGGACCGAAACGGTCTA

TRCB   5'GGGGATCCCATCAGAGACGCTAGACCGTTTCGG where the bold faced sequences in TRSS and TRCB are the restriction endonuclease recognition sequences for the Sal I and Bam HI enzymes, respectively. The oligonucleotides, in a 5:1:0.1:0.1 molar ratio of TRS (5 μg):TRC:TRSS:TRCB, respectively, were added to a mixture containing 15 U of SEQUENASE polymerase and 1× SEQUENASE buffer in a total volume of 15 μl and incubated at 37° C. for 2 hours. To optimize the fill-in reaction, another 10 U of SEQUENASE was added after the first hour of incubation. The mixture was diluted to 150 μl and desalted by spin chromatography through G-50 Sephadexcolumns and reconcentrated to a volume of approximately 15 μl by lyophilization in a Speed-Vac. Nine microliters of the DNA mixture was transfered to another tube containing 1 μl of 10× ligase buffer and 2 U of T4 DNA ligase and incubated at 37° C. for 2 hours to ligate gapped DNA pieces. Two microliters of 10× Sal I digestion buffers 1 μl (5 U) each of Sal I and Bam HI enzyme and 4 μl of water were added and the mixture was incubated at 37° C. for 3 hours. After the restriction digestion, the mixture was subjected to electrophoresis in 0.8% agarose gel. The electrophoresis was performed until the bromphenol blue marker was 1.5 inches into the gel. This separated the cleaved end fragments from the concatameric DNA fragments. After electrophoresis the gel lane containing the DNA was cut from the area just above the bromphenol blue dye band to the area approximately 1 mm below the bottom of the gel loading area. The DNA was electroeluted from the lane and concentrated by precipitation with ethanol. This protocol gives a variety of concatameric sizes which can also be size selected from the agarose gel, if desired. Alternatively, the insert size can be selected after the concatamers are cloned into the RR vector DNA.

Concatameric DNA was cloned into the RR-containing vector described above by mixing the the eluted concatameric DNA with a gel-purified fragment of the RR vctor which had been digested previously with Bam HI and Sal I restriction enzymes. The molar ratio of the vector DNA to insert DNA (as calculated from the original TR concentrations) used in our experiments was 1:100. This gives approximately a 1:2 ratio if the concatamer size averages 2.3 kb. We have found this ratio to give multiple inserts of concatamer and recommend that the ratio be increased to contain at least a 3:1 ratio of vector:insert. We have used this protocol to clone fragments of concatamer which are between 1200 and 1500 nucleotides in length, as judged by restriction analysis and transcription of Bam HI linearized DNA fragments.

After the concatameric cassette is developed, the "self"-cleavage of the TR concatamer by the RR can be checked by incubation of $^{32}$P-labeled, in vitro transcribed ribozyme in the presence of 10 mM $Mg^{+2}$ as described previously. After appropriate times, aliquots should be analyzed by gel elctrophoresis. A successful digestion reaction is exemplified by the disappearance of full-length transcript and accumulation of monomer or multimer length ribozymes over time. After verification of RR activity in vitro the cassette can be excised from the plasmid vector and inserted into a eucaryotic expression vector for intracellular analyses of ribozyme transcription and stability and the cleavage activities of the RR and TR can be assessed.

We have found it preferable to limit the size of the TRC and TRCB oligonucleotides because longer annealing arms decrease the extent of concatamer formation. This cloning portocol may be modified for use with any ribozyme motif, but use of larger inserts limits the number of ribozymes which may be encoded by any transcript because of limitations upon the size of the encoding DNA which may be effectively introduced into cells. If one desires to use multiple ribozymes in the cassettes, then separate mini-cassettes containing the TR concatamer (or monomer) and a corresponding RR should be prepared for incorporation into an expression vector. Use of different 5' and 3' restriction endonuclease sites flanking the individual cassettes would facilitate the cloning into vectors. Because the efficiency of ribozyme release within a cell will depend upon the intracellular salt concentrations, it is preferable to use the same ribozyme motif for the RR as is used for the TR. In this manner, both ribozymes will be active in the same cell types. A preliminary assay of ribozyme activity in cellular extracts is recommended to identify the best cleaving motif for a given target cell type.

Other embodiments are within the following claims.

We claim:

1. A method for in vivo selection of a ribozyme active on a defined RNA target, comprising the steps of:

introducing a first population of ribozymes, in which each said ribozyme has a different substrate binding arm, into a second population of cultured cells, wherein said ribozymes are formed from a third population of fragmented target DNA molecules encoding said RNA target into each of which an enzymatic portion of a ribozyme is inserted;

providing said RNA target to said second population of cultured cells, and identifying those cells which contain a ribozyme active at the RNA target;

wherein said third population is formed by fragmenting target DNA encoding said defined RNA target with DNAseI, and introducing an enzymatic portion of a ribozyme encoding sequence within the fragments generated by said fragmenting by cleaving each said fragment and then ligating said enzymatic portion of a ribozyme encoding sequence into each said fragment.

2. The method of claim 1, wherein said cleaving of each said fragment is by use of a restriction endonuclease.

3. The method of claim 2, wherein said restriction endonuclease recognizes a site outside of said target sequence.

4. The method of claim 2, wherein said restriction endonuclease is selected from the group consisting of BpmI and BsgI.

5. The method of claim 1, wherein said ribozymes are encoded by an expression vector, and said method comprises causing said ribozymes to be expressed from said vector in said cells.

6. The method of claim 1, wherein said RNA target is a viral RNA and said identifying includes determining cell survival after infection of said cells by said viral RNA.

7. The method of claim 1, wherein said RNA target is a mammalian RNA and said cells are mammalian cells.

8. The method of claim 5, wherein said vector comprises sequences encoding a 5' or 3' hairpin or a poly(A) tail for said ribozyme.

9. The method of claim 5, wherein said ribozyme is a hammerhead ribozyme having at least one substrate binding arm comprising between six and eight nucleotides.

10. The method of claim 1, wherein said identifying comprises detecting expression of a reporter RNA attached to or regulated by said RNA target.

11. The method of claim 1, wherein said ribozyme active at the RNA target is recloned into an amphitrophic retrovirus vector.

12. The method of claim 11, wherein a said retrovirus vector having or encoding said ribozyme is selected for ribozyme activity active at said RNA target.

13. The method of claim 1, wherein said first population of ribozymes have the formula 5' NCNA 3' wherein each N is or encodes a ribozyme substrate binding arm, C is or encodes an enzymatic portion of a ribozyme, and A is a polyadenylation sequence; wherein at least one said N in said population differs in each said ribozyme.

14. The method of claim 13, wherein said formula is 5' RNCNAS 3' wherein R and S are restriction endonuclease sites.

15. The method of claim 13, wherein said formula is 5' RLNCNLALS 3' wherein each said L independently is nothing or an insertion region which is or encodes a nuclear processing signal, an RNA stability signal, a splicing signal, or another nucleotide signal which effects transport or stability of said ribozyme molecule.

16. The method of claim 15, wherein said formula is 5' RLCNLALSH 3' where H is a sequence which is or encodes a hairpin ribozyme or a hepatitis delta ribozyme which cleaves 3' of said S.

17. The method of claim 16, wherein said formula is 5' DRLCNLALSE 3' wherein D and E are defined nucleotide sequences which can be used to prime amplification of a said molecule, or the complement of which can be used to prime amplification of a said molecule.

18. The method of claim 17, wherein each N is formed by fragmenting a target DNA and inserting said C within each said fragment.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 1:

CUGAUGAGGC CGAAAGGCCG AAA        2 3

( 2 ) INFORMATION FOR SEQ ID NO: 2:

( i ) SEQUENCE CHARACTERISTICS:
        ( A ) LENGTH: 15
        ( B ) TYPE: nucleic acid
        ( C ) STRANDEDNESS: single
        ( D ) TOPOLOGY: linear ( i i ) SEQUENCE DESCRIPTION: SEQ ID NO: 2:

AUUGGGGUCU GGAUA        1 5

( 2 ) INFORMATION FOR SEQ ID NO: 3:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( i i ) SEQUENCE DESCRIPTION: SEQ ID NO: 3:

UAUCCACUGA UGAGGCCGAA AGGCCGAAAC CCCAAU    3 6